Figure 1:
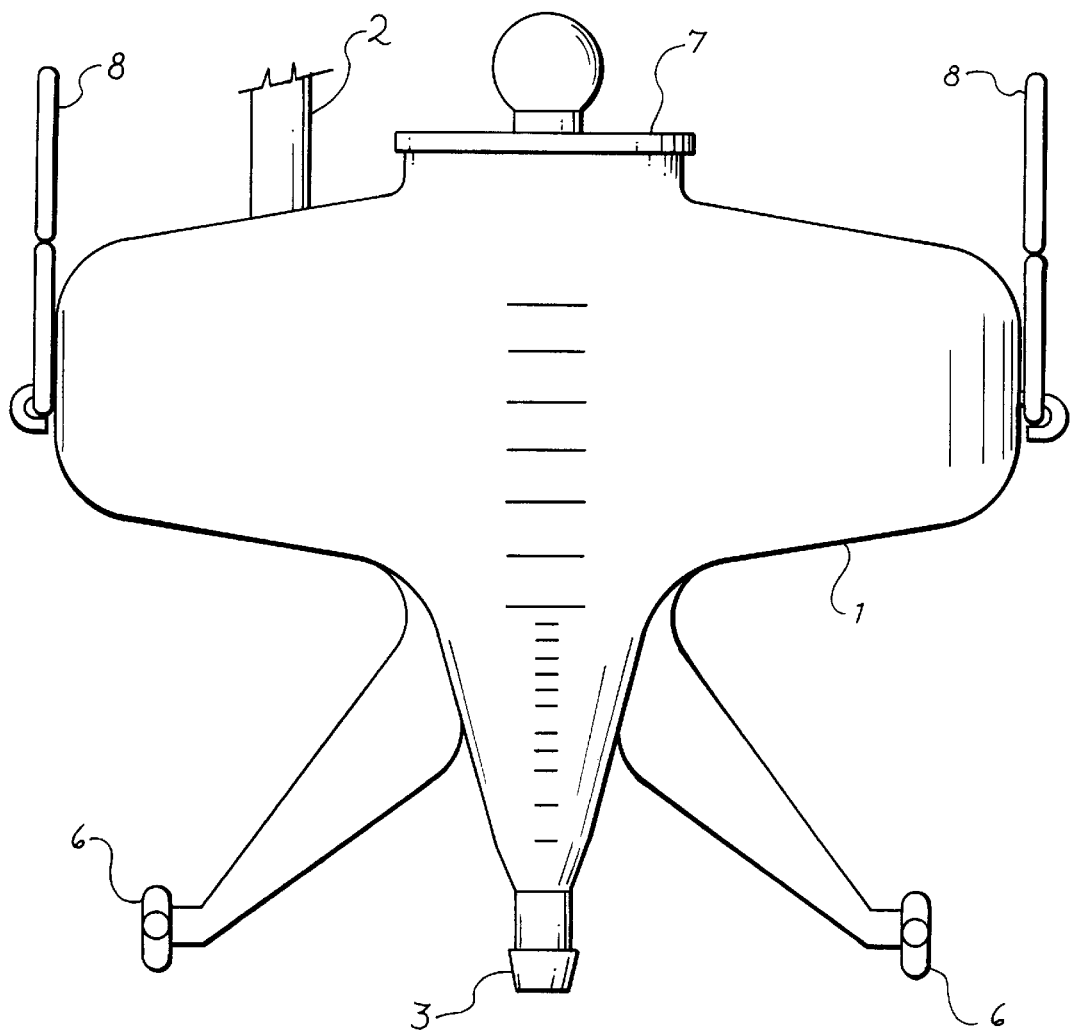

United States Patent
Nielsen et al.

[11] Patent Number: 5,911,786
[45] Date of Patent: Jun. 15, 1999

[54] APPARATUS FOR COLLECTING AND MEASURING BODY FLUID

[75] Inventors: Lars Priess Nielsen, Frederiksberg; Karsten Aakerlund, Hundested, both of Denmark

[73] Assignee: Maersk Medical A/S, Lynge, Denmark

[21] Appl. No.: 08/737,537

[22] Filed: Feb. 10, 1997

[30] Foreign Application Priority Data

May 6, 1994 [DK] Denmark ................................. 530/94

[51] Int. Cl.⁶ .................................................. G01F 19/00
[52] U.S. Cl. ........................... 73/427; 600/584; 604/335
[58] Field of Search ............................ 73/428, 426, 427, 73/864.64; 128/760, 766, 767, 771; 604/323, 335; 600/573, 580, 584

[56] References Cited

U.S. PATENT DOCUMENTS

| | | | |
|---|---|---|---|
| 53,841 | 4/1866 | Lloyd | 73/428 |
| 2,149,303 | 3/1939 | Markwood | 73/426 |
| 3,888,126 | 6/1975 | Cross | 73/426 |
| 3,888,236 | 6/1975 | Marx | 73/427 X |
| 3,961,529 | 6/1976 | Hanifl | 73/427 X |
| 4,002,075 | 1/1977 | Cross | 128/771 X |
| 4,265,118 | 5/1981 | Griesel | 73/427 |
| 4,305,405 | 12/1981 | Meisch | 128/767 X |
| 4,625,734 | 12/1986 | Sherlock et al. | 604/323 X |
| 4,717,388 | 1/1988 | Steer et al. | 604/335 |
| 4,815,477 | 3/1989 | McWhorter et al. | 128/766 |
| 4,854,182 | 8/1989 | Ryan et al. | 73/864.64 |
| 5,084,035 | 1/1992 | Salvadori et al. | 604/323 |
| 5,119,675 | 6/1992 | Mohiuddin | 128/767 X |

FOREIGN PATENT DOCUMENTS

| | | |
|---|---|---|
| 0 008 450 A1 | 8/1979 | European Pat. Off. . |
| WO 89/05119 | 6/1989 | WIPO . |
| WO 95/13016 | 5/1995 | WIPO . |

OTHER PUBLICATIONS

International Search Report of International Application No. PCT/DK 95/00182.

*Primary Examiner*—George M. Dombroske
*Assistant Examiner*—Paul D. Amrozowicz
*Attorney, Agent, or Firm*—Brinks Hofer Gilson & Lione

[57] ABSTRACT

An apparatus for collecting and measuring body fluid comprises a measurement container which is provided with a fluid inlet (2) at its uppermost end and at its lowermost end has a fluid outlet (3) where a rod-shaped valve means (4) is arranged, wherein the measurement container is constructed with an opening in the upper area through which opening the valve means may be activated, a fluid collection bag connected to the fluid outlet and suspended from the measurement container and flexible connecting element (7), e.g. a bellows, which is mounted on the one hand on a rim region of the opening in the measurement container and on the other hand on the valve means, as the flexible connection (7) allows axial movement of the valve manes (4, 5) relative to the measurement container (1).

20 Claims, 2 Drawing Sheets

APPARATUS FOR COLLECTING AND MEASURING BODY FLUID

The present invention relates to an apparatus for collecting and measuring body fluid, said apparatus comprising a measurement container which is provided with a fluid inlet at its uppermost end and at its lowermost end has a fluid outlet where a rod-shaped valve means is arranged, wherein said measurement container is designed with an opening in the upper area through which opening the valve means may be activated. A fluid collection bag is preferably connected to the fluid outlet and suspended from the measurement container.

The apparatus of the type described above is used e.g. in hospitals to monitor the discharge of urine from bedridden patients and in particular from patients having catheters inserted in their urine bladders.

The catheter is connected to the fluid inlet of the measurement container and the measurement container and its urine bag are typically suspended at the patient's bedside. The urine bag may be suspended e.g. from two hooks arranged on carrier arms which protrude from the measurement container. When the patient is transported in his bed from one place to another or is moved into another bed, the measurement container and its urine bag are usually arranged in an inclined position between the patient's legs.

In a known device of the type described above, a rod-shaped valve means extends through an opening in the upper region of the measurement container where the valve means may be activated from the outside of the container by a pull thereby opening it to passage of fluid through the fluid outlet. Therein the sealing between the valve means and the container opening is a slide fit.

However, this construction is inconvenient since sufficient sealing between the shaft and the measurement container makes high demands to the construction and there will be a risk of unwanted intrusion of bacteria and undesirable fluid seepage.

WO 89/05119 shows an apparatus of the type mentioned in the introduction. In this prior art construction the sealing between the container and the valve means is effected by an O-ring and the axial displacement is effected by a turning operation as the valve means are guided in a helical groove. This construction is complicated and therefore relatively expensive to produce. The apparatus comprises a cover for the valve means, which cover in a closed portion for the valve means abuts on the measurement container.

It is thus the object of the present invention to provide an apparatus wherein efficient sealing may be obtained in a more simple manner than previously.

It is a further object of the invention to provide an apparatus whose construction and functioning are more simple that those of the known apparatuses.

These objects are obtained with the apparatus according to the invention, which apparatus is characterised in comprising a flexible fluid and sealing connecting element which in several axially displaced positions for the valve means relative to the measurement container is secured to on the hand to a rim region of the opening in the measurement container and on the other hand to the rod-shaped valve means where the flexible connection element allows axial movement of the valve means relative to the measurement container.

The flexible connection being secured to the container and to the valve shaft, there are no mutually displaceable sealing planes in this area.

When the measurement container is emptied, the valve means is lifted off the valve seat. Hereby passage of fluid is from the measurement container to the fluid outlet and from here to the fluid collection bag.

Thus, in a closed state, the flexible connecting element is advantageously secured on the valve shaft displaced towards the valve means. It will be a further advantage if the flexible connecting element is made of a material whose thickness and rigidity enable the element to influence the valve means with a spring force towards the fluid outlet in a closed position and away from the fluid outlet in an open position of the valve. Hereby the flexible connecting element may be constructed as e.g. a bellows where the cross sections in its extreme positions, i.e. in a closed and a completely open position of the valve, depend on the material length between the securing sites on the container and the valve means, respectively, and moreover on any shape optionally determined in advance. It may for instance be a fraction of a hollow sphere.

According to an advantageous embodiment, the flexible connecting element is made of a material whose thickness and rigidity enable the connecting element to influence the valve means with a spring force towards the fluid outlet in a closed position and away from the fluid outlet in an open position of the valve. Hereby the connecting element assists in ensuring a tight communication between the valve means and the measurement container at the outlet opening.

When the valve is activated, the deformation of the flexible connecting element is most extensive in the rim region at the opening of the measurement container and at the valve means, and in order to limit the tensions within the material, it is thus advantageous that the flexible connecting element be constructed with reduced material thickness in the region around the valve means and in the region around the container opening.

In order to ensure pressure equalization in the container by inflow of fluid, the container is provided with an opening which is covered by an air permeable and fluid-proof filter. To prevent this filter from getting into contact with fluid which may cause it to clog, the filter may particularly conveniently be arranged in connection with a first opening in a hollow valve shaft which faces the environment and which is in communication with the container interior through a second opening in the shaft. The second opening may moreover serve as an overflow opening when the valve shaft is hollow and in communication with the outlet opening. Location of the opening at the shaft end also serves to simplify production of the structure.

The flexible connecting element may be in permanent communication with the container and the valve shaft, e.g. by glueing or welding. Alternatively the flexible connecting element may be releasably secured to at least the measurement container so as to permit dismounting of the valve which in turn allows for suitable cleaning and disinfection of the apparatus with a view to renewed use thereof.

Figure 2:
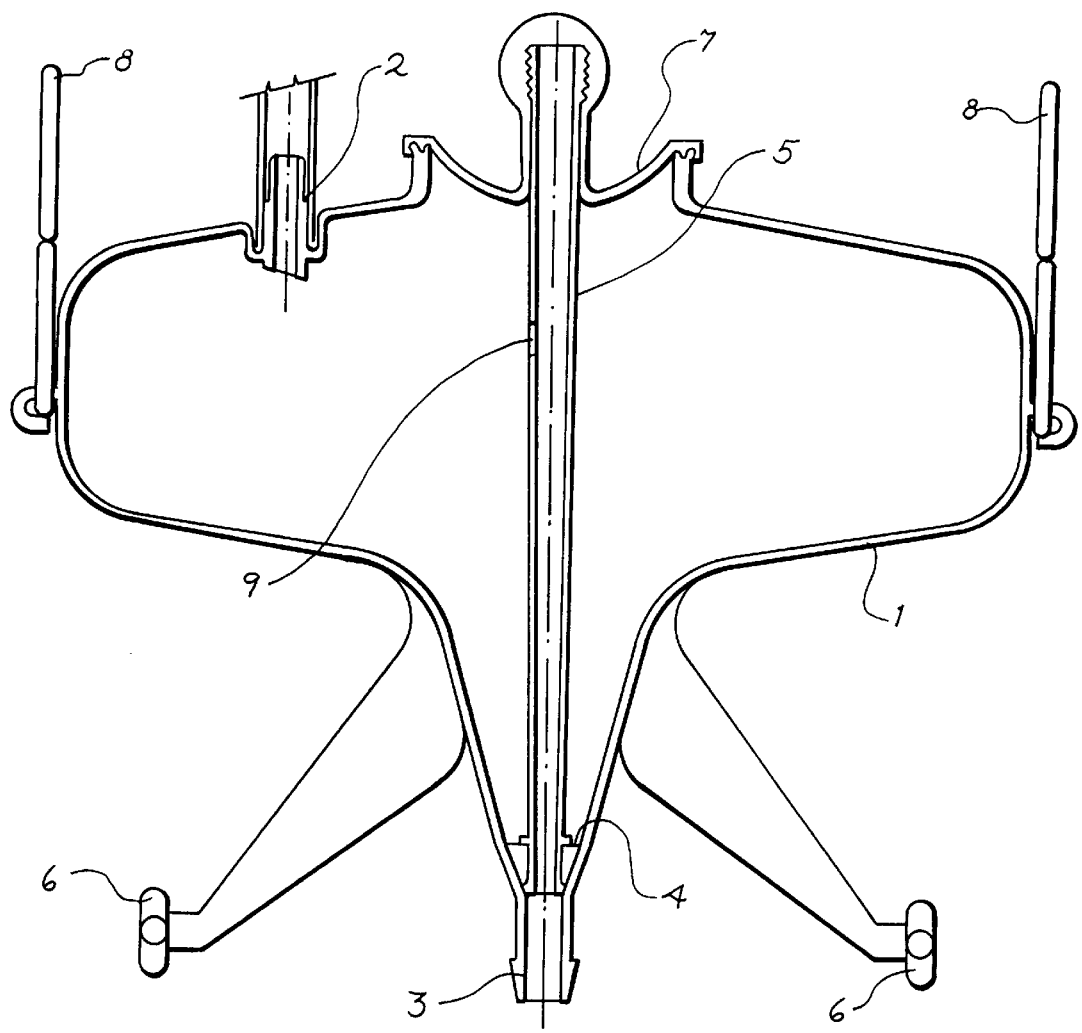
Figure 3:
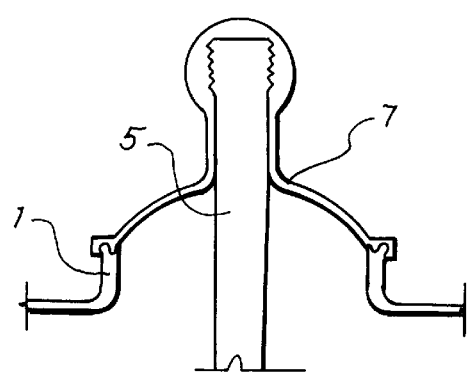

The invention will now be described in further detail with reference to the drawings, wherein FIG. 1 is a front view of an apparatus according to the invention, FIG. 2 is a vertical sectional view of a preferred embodiment of the apparatus according to the invention, FIG. 3 is a vertical sectional view through the flexible communication shown in FIG. 1 in its open position.

FIG. 1 of the drawings shows a urine measurement device consisting of a container 1 having an inlet opening 2 and an outlet opening 3. Preferably the container is calibrated to permit reading of the amount of urine discharged at determined time intervals. In the region at the outlet opening the interior of the container 1 is conical. Thus, the conical portion of the container has a smaller cross sectional area than the portion of the container which is situated thereabove. This allows for a finer measurement scale on the conical portion which then in turn allows for more accurate reading. This is of particular importance in case of postoperative control when the urine discharge is checked at short time intervals.

It will appear from FIG. 2 that a conical body 4 located on a rod element 5 closes the outlet opening 3, the lower portion of the conical portion of the container forming a seat for the valve means. Moreover, the container is so constructed that a (not shown) collection bag may be mounted thereon in connection with the outlet opening. The bag, which is known per se, may be suspended from a pair of carrier arms which end in double pegs 6. The fluid collection bag may be of a type which is provided with a fluid outlet wherein a tube with a valve is inserted.

The rod element 5 with the closing body 4 protrudes through an opening in the upper region of the container 1. Between the rim of the opening and the rod element, a flexible bellows 7 is provided. This bellows 7 serves as a seal to the environment and thus prevents undesirable intrusion of bacteria and fluid seepage. Following reading, the measurement container 1 is emptied by lifting the rod element 5 with the closing body 4 as indicated in FIG. 3 whereby the outlet opening 3 is opened. In connection with the rod element, an overflow communication may optionally be provided by means of a rod which is hollow and provided with an opening 9 to the interior of the container.

It will appear from FIGS. 2 and 3 that the flexible connecting element 7 is releasably connected to the measurement container, the latter being provided with an annular notch for engagement with an also annular rib on the flexible connecting element. In this region, the outside of the measurement container is moreover provided with a thickening around which the flexible connecting element engages with a rim region arranged therefor. Hereby resistance is exerted to prevent the flexible connecting element rib from being pulled out of the notch. It is moreover possible to construct the thickening so as to face the opening area.

The urine measurement and collection device may for instance be suspended from a bed by means of straps 8.

The opening in the upper region of the measurement container where the flexible connecting element is secured is preferably circular. However, it will also be possible to construct the opening with other shapes.

We claim:

1. An apparatus for collecting and measuring body fluid, the apparatus comprising a measurement container (1) which is provided with a fluid inlet (2) at its uppermost end and at its lowermost end has a fluid outlet (3) where a rod-shaped valve means (4,5) is provided, wherein the measurement container is constructed with an opening in an upper area through which opening the valve means may be activated, the apparatus further comprising a flexible connecting element (7) for providing a fluid and air seal which in several axially displaced positions for the valve means relative to the measurement container is secured to a rim region of the opening in the measurement container (1) and to the rod-shaped valve means (4,5), said flexible connecting element (7) permitting axial movement of the valve means (4,5) relative to the measurement container (1).

2. The apparatus according to claim 1, wherein the flexible connecting element (7) is connected to a shaft (5) of the valve means displaced towards the outlet opening in a closed state of the valve means.

3. The apparatus according to claim 1, wherein the flexible connecting element (7) is made of a material whose thickness and rigidity enable the connecting element to influence the valve means (4,5) with a spring force towards the fluid outlet in a closed position and away from the fluid outlet in an open position of the valve.

4. The apparatus according to claim 1, wherein the flexible connecting element (7) is constructed with a reduced material thickness in an area adjacent the valve means (4,5) and in an area adjacent the container opening.

5. The apparatus according to claim 1, wherein the flexible connecting element (7) encloses the end portion of the valve means (4,5) and is provided with means for manual operation of the valve.

6. The apparatus according to claim 1, wherein at least a portion of the valve means (5) is hollow and provided with an opening (9) towards the interior of the measurement container forming an overflow opening for a fluid collection bag for the fluid in the measurement container (1).

7. The apparatus according to claim 1, further comprising an opening which is covered by an air permeable and fluid-sealing filter.

8. The apparatus according to claim 7, wherein the opening is provided at the end of the valve shaft (5).

9. The apparatus according to claim 1, wherein the flexible connecting element (7) is permanently secured to the container (1) and the valve shaft (5).

10. The apparatus according to claim 1, wherein the flexible connecting element (7) is releasably secured to at least the measurement container (1).

11. The apparatus according to claim 2, wherein the flexible connecting element (7) is made of a material whose thickness and rigidity enable the connecting element to influence the valve means (4,5) with a spring force towards the fluid outlet in a closed position and away from the fluid outlet in an open position of the valve.

12. The apparatus according to claim 2, wherein the flexible connecting element (7) is constructed with a reduced material thickness in an area adjacent the valve means (4,5) and in an area adjacent the container opening.

13. The apparatus according to claim 3, wherein the flexible connecting element (7) is constructed with a reduced material thickness in an area adjacent the valve means (4,5) and in an area adjacent the container opening.

14. The apparatus according to claim 2, wherein the flexible connecting element (7) encloses the end portion of the valve means (4,5) and is provided with means for manual operation of the valve.

15. The apparatus according to claim 4, wherein the flexible connecting element (7) encloses the end portion of the valve means (4,5) and is provided with means for manual operation of the valve.

16. The apparatus according to claim 2, wherein at least a portion of the valve means (5) is hollow and provided with an opening (9) towards the interior of the measurement container forming an overflow opening for a fluid collection bag for the fluid in the measurement container (1).

17. The apparatus according to claim 5, wherein at least a portion of the valve means (5) is hollow and provided with an opening (9) towards the interior of the measurement container forming an overflow opening for a fluid collection bag for the fluid in the measurement container (1).

18. The apparatus according to claim 2, further comprising an opening which is covered by an air permeable and fluid-sealing filter.

19. The apparatus according to claim 6, further comprising an opening which is covered by an air permeable and fluid-sealing filter.

20. The apparatus according to claim 8, wherein the flexible connecting element (7) is permanently secured to the container (1) and the valve shaft (5).

* * * * *

UNITED STATES PATENT AND TRADEMARK OFFICE
CERTIFICATE OF CORRECTION

PATENT NO. :     5,911,786
DATED      :     June 15, 1999
INVENTOR(S) :    Lars P. Nielsen et al.

It is certified that error appears in the above-identified patent and that said Letters Patent is hereby corrected as shown below:

On the Title Page

In column 2, line 13, under "ABSTRACT", please change "manes" to --means--.

Signed and Sealed this

Seventeenth Day of April, 2001

Attest:

NICHOLAS P. GODICI

*Attesting Officer*   *Acting Director of the United States Patent and Trademark Office*